United States Patent [19]

Corley

[11] Patent Number: 5,300,603
[45] Date of Patent: Apr. 5, 1994

[54] DIALKYLIDENECYCLOBUTANE/ACRYLATE/BIS-MALEIMIDE COMPOSITION

[75] Inventor: Larry S. Corley, Houston, Tex.

[73] Assignee: Shell Oil Company, Houston, Tex.

[21] Appl. No.: 64,561

[22] Filed: May 19, 1993

Related U.S. Application Data

[60] Division of Ser. No. 890,059, May 28, 1992, Pat. No. 5,250,643, which is a continuation-in-part of Ser. No. 733,947, Jul. 22, 1991, Pat. No. 5,147,953.

[51] Int. Cl.$^5$ .............................................. C08F 22/40
[52] U.S. Cl. .................................. 526/262; 524/548; 524/559; 524/560; 526/308; 528/322
[58] Field of Search ............... 526/262, 308; 528/322; 524/548, 559, 560

[56] References Cited

U.S. PATENT DOCUMENTS

| | | | |
|---|---|---|---|
| 4,645,814 | 2/1987 | Grubbs | 526/252 |
| 4,730,030 | 3/1988 | Hahn et al. | 526/262 |
| 4,973,636 | 11/1990 | Corley | 526/262 |
| 5,147,953 | 9/1992 | Corley | 526/262 |

OTHER PUBLICATIONS

Godt et al., "Double-Stranded Molecules," *Angew. Chem.* 28, 1680–1682 (1989).

*Primary Examiner*—Harold D. Anderson

[57] ABSTRACT

A composition comprising a 1,2-dialkylidenecyclobutane such as 1,2-dimethylenecyclobutane, a polyacrylate monomer and an optional polyimide such as a bis-maleimide can be thermally cured to a tough copolymer having a high glass transition temperature.

16 Claims, No Drawings

DIALKYLIDENECYCLOBUTANE/ACRYLATE/- BIS-MALEIMIDE COMPOSITION

CROSS-REFERENCE TO RELATED APPLICATION

This is a division of application Ser. No. 07/890,059, filed May 28, 1992, now U.S. Pat. No. 5,250,643, which was a continuation-in-part of application Ser. No. 07/733,947, filed Jul. 22, 1991, now U.S. Pat. No. 5,147,953.

BACKGROUND OF THE INVENTION

This invention relates to thermosettable resin compositions. In one embodiment, the invention relates to enhancement of the properties of acrylic and bisimide/acrylic compositions.

Advanced composites are high-performance materials made up of a fiber-reinforced thermoplastic or thermosettable material. Thermosettable materials useful in advanced composites applications must meet a set of demanding property requirements. For example, such materials optimally have good high-temperature properties such as high (above 200° C.) cured glass transition temperature and good mechanical strength. For ease of processing in preparing prepregs for composite parts, the uncured material will ideally have a low (below 120° C.) melting temperature and a wide temperature range of processable viscosity (a wide "processing window").

Polymers of multifunctional acrylic monomers tend to be very brittle, especially if high in Tg. Bismaleimide resins have superior high-temperature properties but are also very brittle and further tend, because of their high softening points, to require solvents in order to be readily processable. In addition, standard cured bismaleimide resins tend to have high (in the 5-7% range) 93° C. water absorption. Addition of thermoplastic or cyanate-terminated oligomers increases the toughness but produces uncured mixtures so high in viscosity that fiber impregnation and processing by standard thermoset techniques are difficult.

It is thus an object of the invention to provide new thermoset resin materials. In one aspect, it is an object of the invention to provide comonomers which provide low-melting bismaleimides which cure to high-Tg, tough resins. In one embodiment, it is an object of the invention to provide toughened polymers of multifunctional acrylic monomers.

SUMMARY OF THE INVENTION

According to the invention, a composition is provided comprising a 1,2-dialkylidenecyclobutane and a difunctional or polyfunctional acrylic monomer. According to one aspect of the invention, the composition further comprises a polyimide. The invention copolymers have superior toughness and can be melt-processed for composites applications.

DETAILED DESCRIPTION OF THE INVENTION

The invention composition optionally includes a bisimide of an unsaturated dicarboxylic acid. The preferred bisimides are N,N'-bisimides of unsaturated dicarboxylic acids which can be represented by the formula

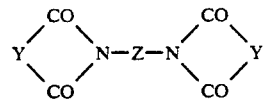

in which Y is a substituted or unsubstituted divalent group containing at least 2 carbon atoms, preferably 2 to 6 carbon atoms, and a carbon-carbon double bond, and Z is a divalent group containing at least 1 and generally about 1 to 40 carbon atoms. Z can be aliphatic, cycloaliphatic, aromatic or heterocyclic. A preferred class of bisimides comprises bismaleimides derived from aromatic amines and can be represented by the formula

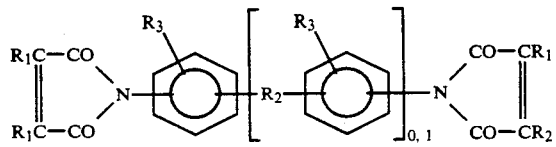

in which each $R_1$ is selected independently from H, $C_{1-2}$ alkyl or halide; $R_2$ is selected from divalent hydrocarbon radicals containing from about 1 to about 10 carbon atoms, —O—, —$SO_2$—, —COO—, —CONH—, —CO— and —S—; and each $R_3$ is selected independently from H, $C_{1-3}$ alkyl and halide. The aromatic rings may alternatively be heterocyclic.

Examples of such bisimides include
1,2-bismaleimidoethane
1,6-bismaleimidohexane
1,3-bismaleimidobenzene
1,4-bismaleimidobenzene
2,4-bismaleimidotoluene
4,4'-bismaleimidodiphenylmethane
4,4'-bismaleimidodiphenylether
3,3'-bismaleimidodiphenylsulfone
4,4'-bismaleimidodiphenylsulfone
4,4'-bismaleimidodicyclohexylmethane
3,5-bis(4-maleimidophenyl)pyridine
2,6-bismaleimidopyridine
1,3-bis(maleimidomethyl)cyclohexane
1,3-bis(maleimidomethyl)benzene
1,1-bis(4-maleimidophenyl)cyclohexane
1,3-bis(dichloromaleimido)benzene
4,4'-biscitraconimidodiphenylmethane
2,2-bis(4-maleimidophenyl)propane
1-phenyl-1,1-bis(4-maleimidophenyl)ethane
α,α-bis(4-maleimidophenyl)toluene
3,5-bismaleimido-1,2,4-triazole
and various N,N'-bismaleimides disclosed in U.S. Pat. Nos. 3,562,223, 4,211,860 and 4,211,861. Bismaleimides can be prepared by methods known in the art, as described in U.S. Pat. No. 3,018,290, for example.

The bisimide resin can contain imide oligomers according to the formula

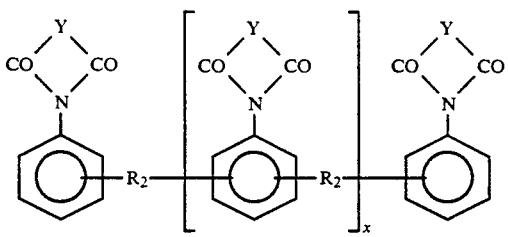

in which x is a number within the range of about 0 to about 3. Such oligomers may be present as an impurity in difunctional bisimides.

The preferred bisimide resin is 4,4'-bismaleimidophenylmethane. Suitable N,N'-unsaturated bismaleimideresins are commercially available from Technochemie GmbH as Compimide ® resins, for example.

The invention composition includes a1,2-dialkylidenecyclobutane, including those which can be described by the structural formula

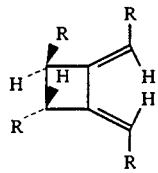

in which each R is selected independently from hydrogen, $C_{1-10}$ alkyl, halo, aryl, alkoxy, aryloxy, alkylthio, arylthio and dialkylamino. The presently preferred 1,2-dialkylidenecyclobutane, because of the superior properties of a bisimide copolymer prepared therewith, is 1,2-dimethylenecyclobutane, which is defined by the above formula when each R is hydrogen.

In general, dialkylidenecyclobutanes can be prepared by the thermal dimerization of the corresponding allenes in a recirculating hot-tube reactor. Specifically, the process will generally be carried out by circulating a stream of gaseous allene through a tube reactor at 450°–600° C. with a residence time in the hot zone of 0.1 to 10 seconds. Downstream from the hot zone, the stream is cooled sufficiently to condense the dialkylidenecyclobutane. Unchanged allene (combined with a fresh makeup stream) is recirculated back to the hot zone by a pump. Such a process is described for 1,2-dimethylenecyclobutane in Chernykh et al., Neftepererab. Neftekhim. 1981 (7), 48–50. Synthesis of 1,2-dimethylenecyclobutane is also illustrated in Example 1 herein. The allene starting material can be produced by pyrolysis of isobutylene or by isolation from a hydrocarbon mixture such as a refinery cracker stream.

The invention composition includes a polyfunctional acrylic monomer (which will be referred to herein as the "polyacrylate monomer") including the polyacrylate and polymethacrylate esters of polyols containing more than one terminal acrylate or methacrylate group. These esters are the acrylic and methacrylic acid esters of aliphatic polyhydric alcohols such as, for example, the di- and polyacrylates and the di- and polymethacrylates of alkylene glycols, polyoxyalkylene glycols, alicyclic glycols and higher polyols, such as ethylene glycol, triethylene glycol, tetraethylene glycol, tetramethylene glycol, hexanediol, trimethylolethane, trimethylolpropane, pentaerythritol, dipentaerythritol, tripentaerythritol and the like; or mixtures of these with each other or with their partially esterified analogs.

Typical polyacrylate monomers include but are not limited to trimethylolpropane triacrylate, trimethylolethane triacrylate, trimethylolpropane trimethacrylate, trimethylolethane trimethacrylate, tetramethylene glycol dimethacrylate, ethylene glycol dimethacrylate, triethylene glycol dimethacrylate, pentaerythritol triacrylate, pentaerythritol tetraacrylate, 1,6-hexanediol diacrylate, 1,6-hexanediol dimethacrylate, dipentaerythritol tetraacrylate, dipentaerythritol pentaacrylate, and the like. Particularly preferred polyacrylates are neopentyl glycol dimethacrylate, trimethylolpropane trimethacrylate, trimethylolpropane triacrylate, pentaerythritol triacrylate, and 1,3-butylene dimethacrylate.

In general, polyacrylates are preferred to polymethacrylates, because polyacrylates react into the network more readily than polymethacrylates and also tend to be better solvents for the other components. Difunctional acrylates tend in general to give tougher castings than multifunctional acrylates.

The 1,2-dialkylidenecyclobutane and polyacrylate and optional polyimide monomers may be combined in any manner desired, such as melt, solution or powder blending. The preferred technique, when sufficiently large quantities of monomers are used, involves heating a mixture of the polyacrylate, the liquid 1,2-dialkylidenecyclobutane and, if used, the polyimide with stirring at a temperature above the respective melting points but below the homopolymerization temperature of any monomer, until the mixture becomes a homogeneous melt. The melt may optionally be held at temperatures above about 140° C. for desired periods of time in a process of prepolymerization to increase the crystallization resistance of the melt and/or to increase its viscosity to desired levels. The mixture can then be poured directly into a mold for polymerization, or it can be cooled for later polymerization. For small quantities of monomers, however, excessive amounts of the dialkylidenecyclobutane may volatilize during the melt reaction, upsetting the desired stoichiometric balance. In these cases, it is preferable for the monomer mixture to be processed in a two-step process in which the monomer mixture is reacted in a solvent, with the solvent then evaporated and the adduct melted and cured to solid polymer without solvent.

The relative amounts of the monomers will depend upon the cured and uncured properties desired. In general, optimum properties will be achieved with a dialkylidenecyclobutane:(acrylate groups+imide groups) equivalent ratio within the range of about 0.5:1 to about 2:1, preferably about 0.8:1 to about 1.2:1, where each mole of dialkylidenecyclobutane is considered 2 equivalents. (If methacrylates rather than acrylates are used, higher ratios relative to dialkylidenecyclobutane are preferred because of their less complete participation in the Diels-Alder reaction.)

The composition may contain an optional free radical inhibitor to inhibit free radical polymerization of the bisimide monomer. Generally, the free radical inhibitor will be present in the composition in an amount within the range of about 0.0002 to about 0.02 moles per mole of the bisimide, preferably from about 0.001 to about 0.01 moles. The free radical inhibitor can be added to the monomers in any manner effective for intimate blending of the monomers and free radical inhibitor. Free radical inhibitors include phenols such as t-butylcatechol, hydroquinone and p-methoxyphenol; quinones such as 1,4-benzoquinone and 1,4-naphthoquinone; polynitro aromatics such as picric acid and 2,4,6-trinitrotoluene; hydroxylamines such as diethylhydroxylamine; stable radicals such as di-t-butylnitroxide or diphenylpicrylhydrazyl; and certain polycyclic heterocycles such as phenothiazine. The preferred free radical inhibitor is phenothiazine.

The invention composition optionally contains a free radical initiator for the polyacrylate monomer. Examples of such initiators include peroxides such as benzoyl peroxide, tertiary butyl hydroperoxide, ditertiary butyl peroxide, hydrogen peroxide, potassium peroxydisulfate, bis(methylcyclohexyl)peroxide, cumene hydroperoxide, acetyl benzoyl peroxide, Tetralin hydroperoxide, phenylcyclohexane hydroperoxide, tertiary butyl peroxyacetate, dicumyl peroxide, tertiary butyl peroxybenzoate, tertiary butyl peroxy(2-ethylhexanoate) and 2,5-bis(tertiary butyl peroxy)-2,5-dimethylhexane and the like, and mixtures thereof; and azo compounds such as 2,2'-azobisisobutyronitrile, dimethyl 2,2'-azobisisobutyrate, 2,2'-azobis(2,4-dimethylvaleronitrile), 2,2'-azobisisobutyramide, 2,2'-azobis(2-acetoxypropane), and the like.

Polymerization is effected by heating the mixture to a temperature effective to initiate opening of the cyclobutene ring (formed by the initial Diels-Alder reaction of the diene group of the dialkylidenecyclobutane with the dienophilic double bond) to form a transient diene which rapidly reacts with available maleimide groups. This temperature is generally at least about 150° C., preferably about 180° to about 350° C., held for a time of about 0.5 hour or more (with the required cure time dependent on the temperature-staging program used).

In order to achieve optimum properties, a mixture of the monomers and free radical inhibitor is heated at a temperature near or above the ultimate (fully-cured) glass transition temperature of the copolymer for a time sufficient to achieve essentially complete reaction of the monomers. "Essentially complete" reaction of the monomers has been reached when no further reaction exotherm is observed by differential scanning calorimetry (DSC) upon heating the copolymer. The time of the heat treatment, or "post-cure," will vary depending upon the monomers, the degree of pressure applied and any pre-curing of the monomer mixture. Preferably, this post-cure is at or above the ultimate Tg, but will always be at a temperature lower than the temperature at which degradation of the copolymer will occur at significant rates.

The copolymers and polymer blends are useful in adhesives, coatings and as resin matrices for composites in aerospace and electronics applications, including large structural parts and circuit boards. Based on their long shelf life and relatively low melting point, some of the uncured mixtures are useful for making tacky prepregs which can then be molded into composites. They are also suitable for low-solvent-or solventless liquid resin processing methods such as filament winding, resin transfer molding and pultrusion if the mixtures are heated to provide sufficiently low viscosity for fiber impregnation. If the monomer mixtures are prepared so as to avoid crosslinking, they can also be used as injection-moldable thermoplastics.

Electrical applications for the invention compositions include encapsulation of electronic devices and electrical lamination for circuit board manufacture. In encapsulation, the composition will usually be combined, generally by melt-blending, with a suitable inert filler such as particulate silica. For lamination, the composition will be applied, in organic solution or in a solventless melt, to a suitable reinforcement such as glass fiber, and partially cured to form an electrical prepreg, which will subsequently be fabricated into a fully-cured laminate.

For preparation of reinforced laminate materials, a fibrous substrate of glass, carbon, quartz, poly(p-phenyleneterephthalamide), polyester, polytetrafluoroethylene, poly(p-phenylenebenzobisthiazole), boron, paper or like material, in chopped, mat or woven form, is impregnated with a dialkylidenecyclobutane/acrylic composition in molten or solution form. A prepreg is formed by heating the impregnated substrate in an oven at a temperature sufficient to remove the solvent and to partially cure without gelation, or "B-stage," the resin system, generally about 120° C. to about 180° C., preferably about 135° to about 175° C., for a time of up to about 2 hours, preferably about 10 to about 40 minutes. A laminate is fabricated by subjecting a set of layered prepregs to conditions effective to cure the resins and to integrate the prepregs into a laminated structure. The laminate can optionally include one or more layers of a conductive material such as copper.

Laminating generally involves subjecting the prepregs to a temperature above about 175° C., preferably from about 180° to about 350° C., for a time of at least about 10 minutes, at a pressure within the range of about 50 to about 500 psi.

For some laminating applications, it may be advantageous to heat treat, or upstage, the monomer mixture prior to application to a laminating substrate, particularly if the mixture will be stored prior to use. Suitable heat treatment involves subjecting the mixture to an elevated temperature for a time sufficient to cause sufficient reaction and viscosity increase to inhibit crystallization of either or both monomers from the mixture upon storage, but not sufficient to gel the composition. Such heat treatment conditions generally include a temperature of at least about 120° C., preferably about 135° to about 175° C., for a time of at least about 10 minutes, preferably about 12 to about 90 minutes. The resulting mixture will be less tacky and less susceptible to crystallization of the components with storage.

EXAMPLE 1

Preparation of 1,2-Dimethylenecyclobutane

A recirculating apparatus for the thermal dimerization of allene was designed as follows. The heated reactor was a bank of approximately 110 segments (each about 30 cm long) of stainless steel tubing 1.27 cm in outside diameter. The segments were arranged vertically in series and connected to one another by U-shaped stainless steel connectors to which they were welded. The volume of the heated portion of the reactor was about 3.4 liters. The bank of tubes was immersed in a fluidized bed of aluminum oxide particles. Thermocouples wedged between the connectors of the reactor at various points allowed one to monitor the wall temperature of different segments of the reactor.

Downstream from the reactor was a cold trap containing a cooling fluid at approximately $-65°$ C. above a flask which functioned as a gas-liquid separator. Downstream from the first trap was a second trap filled with dry ice in dichloromethane, guarding the outlet to the system (through an oil bubbler) to condense any allene which otherwise could have escaped from the system. Condensed allene from this second trap fell into the gas-liquid separator. The condensed material (allene dimers and some of the allene) from the traps fell to the bottom of the separator and then flowed through a fluoropolymer tube into a reservoir for liquid allene and allene dimers. Sufficient heat was applied to this reservoir to keep the allene boiling gently. The allene not condensed by the cold traps was combined with that evaporating from the reservoir. This stream of recovered allene was passed through a filter into a diaphragm pump which recirculated the allene back into the hot tube. A makeup stream of fresh allene from a cylinder was also introduced into the loop just upstream from the recirculation pump.

The system was first purged with nitrogen. The power to the fluidized bed was turned on and its temperature was brought to 450°–470° C. Allene was introduced into the system from the allene cylinder at a rate of 80–100 g/hr. The allene supply from the cylinder was shut off two to three hours before the end of a dimerization run in order that the allene present in the system could be used up, with little allene remaining in the reservoir at the end. At the end of the day, the power to the fluidized bed was turned off, the system was allowed to cool, and the accumulated dimer was poured into a bottle and weighed. Approximately 3 g of phenothiazine was added per kilogram of dimer to inhibit polymerization of the 1,2-dimethylenecyclobutane. The crude dimer was then analyzed by gas chromatography for peaks corresponding to two allene dimers, 1,2-dimethylenecyclobutane (1,2-DMCB) and 1,3-dimethylenecyclobutene (1,3-DMCB), and a component shown by mass spectrometry to have a molecular formula of $C_9H_{12}$ (an allene trimer). Data from seven hot tube reaction runs are shown in Table 1.

enable the preparation of void-free castings) along with 180 grams of dichloromethane solvent. The bottles were placed on rollers and rolled overnight (or longer) at room temperature to allow completion of the first-stage Diels-Alder reaction between the 1,2-dimethylenecyclobutane and the maleimide groups of the bismaleimide. The acrylic monomer (neopentyl glycol diacrylate, trimethylolpropane triacrylate or trimethylolpropane trimethacrylate) and, if used, the high-temperature radical initiator (Atochem Luazo AP, 2,2'-azobis(2-acetoxypropane)) were added to the mixtures at this point and mixed until homogeneous. The mixtures were poured into 250-mL Erlenmeyer flasks with a vacuum connection. The flasks were placed in a 125°–150° C. oil bath and the contents were swirled as solvent, 1,3-dimethylenecyclobutane, and other volatile unreacted materials were removed, first at atmospheric pressure and then under mechanical pump vacuum for a few minutes until bubbling had essentially stopped. The degassed molten mixtures were then poured into a two-piece rectangular stainless steel mold with a ⅛" (3.175 mm) thick cavity, with the mold parts separated by a gastight silicone rubber gasket such that the mold could be pressurized during cure. A few grams of each uncured sample were kept as a retain for characterization of uncured properties. The mold was then placed into an oven and pressurized with nitrogen to 750 kPa (~95 psig) and the systems were cured for one hour at 150° C., followed by ramping linearly to 290° C. over a period of 3.5 hours and then holding for one hour at 290° C. Properties of the castings (and the uncured systems) are shown in Table 2.

One can see from Table 2 that incorporation of acrylic monomers into the BMI-DMCB composition lowers the temperature at which a desirable fiber impregnation viscosity of 1 Pa·s is reached. The uncured

TABLE 1

| | | | | | GC analysis | | |
|---|---|---|---|---|---|---|---|
| Reaction # | Reaction time, hr. | Allene used, g | Crude dimer produced, g | Crude yield, % | 1,3-DMCB, % | 1,2-DMCB, % | $C_9H_{12}$ peak, % |
| 1 | 8.0 | 558 | 443 | 79.4 | 8.4 | 67.0 | 15.0 |
| 2 | 15.8 | 1197 | 881 | 73.6 | 8.1 | 75.0 | 11.0 |
| 3 | 11.3 | 862 | 753 | 87.3 | 8.3 | 73.4 | 11.4 |
| 4 | 11.2 | 824 | 647 | 78.5 | 8.3 | 71.6 | 14.0 |
| 5 | 11.8 | 932 | 806 | 86.5 | 8.5 | 68.7 | 15.4 |
| 6 | 11.4 | 909 | 746 | 82.1 | 8.4 | 68.0 | 16.2 |
| 7 | 11.0 | 872 | 724 | 83.0 | 8.5 | 69.0 | 15.7 |

The products of the seven runs in Table 1 were flash-distilled under vacuum to remove tars and were subsequently distilled under reduced pressure in 2.54 cm Oldershaw columns with 30 plates. The resulting distilled fractions and similarly-obtained DMCB cuts were used in the following examples.

EXAMPLE 2

Preparation of Copolymer of 1,2-Dimethylenecyclobutane, Bismaleimide and Polyacrylate Five mixtures (mixtures 1–2 in Table 2 below) were prepared as follows. To 500-mL glass bottles were added the amounts shown of COMPIMIDE ® 353A (a commercial mixture of the bismaleimide of 4,4'-methylenedianiline with other bismaleimides), a distilled dimethylenecyclobutane fraction containing mostly 1,2-isomer, phenothiazine and Monsanto PC-1344 defoamer (an acrylic oligomer, added to prevent excessive foaming during vacuum degassing and to materials containing acrylate diluents were pliable at room temperature, although cured Tg was lowered. The trimethylolpropane trimethacrylate diluent, although less effective in lowering viscosity, produced little or no loss of cured Tg. Even though acrylic monomer addition produced loss of toughness, all the BMI/DMCB/acrylic blends had fracture toughness values well over 1, and one casting over 2, MPa·m½ (considerably tougher than standard epoxy or bismaleimide resin systems used for composites). All of the acrylic monomers reduced dielectric constant and water pickup of the cured castings.

EXAMPLE 3

Preparation of a Copolymer of 1,2-Dimethylenecyclobutane and a Diacrylate.

Into a glass vial were weighed 11.31 grams (50.0 millimoles) of 1,6-hexanediol diacrylate, 0.0539 grams (0.27 millimoles) of phenothiazine, and 4.80 grams (4.01 grams, or 50.1 millimoles, of 1,2-isomer) of a distilled cut of 1,2-dimethylenecyclobutane containing (by gas chromatography) 83.6% of 1,2-dimethylenecyclobutane and 13.3% of 1,3-dimethylenecyclobutane. The mixture was heated for 17 hours at 75° C. in order to form the initial liquid mixture of Diels-Alder adducts between much of the 1,2-dimethylencyclobutane and the diacrylate. The mixture, after overnight heating, was poured into a 25-mL Erlenmeyer flask with a vacuum connection. The flask was then placed into an 80° C. oil bath and the mixture was degassed under vacuum to remove 1,3-dimethylenecyclobutane and other volatile unreacted materials. The degassed mixture was then poured into a two-piece rectangular stainless steel mold with a 1/16" (1.59 mm) thick cavity, with the mold parts separated by an airtight rubber gasket such that the mold could be pressurized during cure. The mold was then placed into an oven and pressurized with nitrogen to 750 kPa (~95 psig) and the mixture was cured for one hour at 150° C., one hour at 175° C., and one hour at 200° C. The resultant rubbery casting was then removed from the mold. It was then postcured between glass plates for 30 minutes at 230° C., 30 minutes at 250° C., 30 minutes at 270° C., and one hour at 290° C. The resultant cured casting was tough and leathery. Extraction with dichloromethane for two days at room temperature, followed by drying of the residue, showed a gel content of 69% for the casting. A control casting was prepared from a mixture of 16.97 grams (75.0 millimoles) of 1,6-hexanediol diacrylate and 0.0826 grams (0.41 millimoles) of phenothiazine. The solution was degassed in an 80° C. oil bath as above and then cured, under 750 kPa nitrogen pressure in the same mold as the above mixture, for one hour at 150° C., one hour at 180° C., one hour at 210° C., 30 minutes at 230° C., 30 minutes at 250° C., 30 minutes at 270° C., and one hour at 290° C. The resultant casting was so brittle that it crumbled upon attempted removal from the mold.

EXAMPLE 4

Preparation of a Copolymer of 1,2-Dimethylenecyclobutane and a Triacrylate

Into a glass vial were weighed 9.88 grams (33.3 millimoles) of trimethylolpropane triacrylate, 0.0539 grams (0.27 millimoles) of phenothiazine, and 4.80 grams (4.01 grams, or 50.1 millimoles, of 1,2-isomer) of a distilled cut of 1,2-dimethylenecyclobutane containing (by gas chromatography) 83.6% of 1,2-dimethylenecyclobutane and 13.3% of 1,3-dimethylenecyclobutane. The mixture was heated overnight at 75° C. in order to form the initial liquid mixture of Diels-Alder adducts between much of the 1,2-dimethylenecyclobutane and the triacrylate. The mixture, after overnight heating, was poured into a 125-mL Erlenmeyer flask with a vacuum connection. The flask was then placed into an 80° C. oil bath and the mixture was degassed under vacuum to remove 1,3-dimethylenecyclobutane and other volatile unreacted materials. The degassed mixture was then poured into the same stainless steel pressure mold used in Example 3. The mold was then placed into an oven and pressurized with nitrogen to 750 kPa (~95 psig) and the mixture was cured for one hour at 150° C., one hour at 180° C., one hour at 210° C., 30 minutes at 230° C., 30 minutes at 250° C., 30 minutes at 270° C., and one hour at 290° C. The resultant cured casting of hard polymer was sufficiently tough that a sliver could be cut from it with scissors. Dynamic mechanical analysis (Rheometrics) showed a tan δ peak (dynamic mechanical Tg) at 99° C. The compact tension fracture toughness (ASTM E 399-83) was 0.38 MPa-m$^{\frac{1}{2}}$. A control casting was prepared from a mixture of 14.82 grams (50.0 millimoles) of trimethylolpropane triacrylate and 0.0823 grams (0.41 millimoles) of phenothiazine. The solution was degassed in an 80° C. oil bath as above and then cured, under 750 kPa nitrogen pressure in the same mold as the above mixture, by the same cure schedule as above. The resultant casting was so brittle that it crumbled upon attempted removal from the mold.

TABLE 2

| Experiment # | 1 | 2 | 3 | 4 | 5 |
|---|---|---|---|---|---|
| Composition: | | | | | |
| COMPIMIDE ® 353A, grams | 80 | 60 | 60 | 80 | 80 |
| total moles BMI's | 0.2433 | 0.1825 | 0.1825 | 0.2433 | 0.2433 |
| 1,2-Dimethylenecyclobutane (DMCB): | | | | | |
| Crude distillate, grams | 23.60 | 26.12 | 26.12 | 24.25 | 24.25 |
| % 1,2-isomer in crude distillate (GC area) | 82.606 | 83.96 | 83.96 | 80.391 | 80.391 |
| Net 1,2-isomer, | | | | | |
| grams | 19.50 | 21.93 | 21.93 | 19.49 | 19.49 |
| moles | 0.2433 | 0.2737 | 0.2737 | 0.2433 | 0.2433 |
| Neopentyl glycol diacrylate (NPGDA), | | | | | |
| grams | | 19.36 | | | |
| moles | 0.0912 | | | | |
| Trimethylolpropane triacrylate (TMPTA), | | | | | |
| grams | | | 18.02 | | |
| moles | | | 0.0608 | | |
| Trimethylolpropane trimethacrylate, (TMPTMA), | | | | | |
| grams | | | | 10 | 20 |
| moles | | | | 0.0296 | 0.0591 |
| Initiator, grams | | | | 0.10 | 0.10 |
| Phenothizine, grams | 0.23 | 0.20 | 0.20 | 0.23 | 0.23 |
| Defoamer, grams | 0.26 | 0.20 | 0.20 | 0.26 | 0.26 |
| Weight % non (DMCB-BMI), basis total solids$^a$ | 0 | 26.9 | 25.9 | 9.4 | 17.0 |
| Uncured properties: | | | | | |
| Temperature, °C., at which viscosity reaches 1 Pa · s on heatup | 124 | 103 | 101 | 109 | 120 |
| Pliable at room temperature? | No | Yes | Yes | No | No |
| Cured properties: | | | | | |

TABLE 2-continued

| Experiment # | 1 | 2 | 3 | 4 | 5 |
|---|---|---|---|---|---|
| Rheometrics tan δ peak, °C. | 264 | 195 | 215 | 267 | 257 |
| R.T. dry flexural (ASTM D-790): | | | | | |
| Yield strength, MPa | 139 ± 1 | 140 ± 9 | 79 ± 1 | 107 ± 8 | 123 ± 31 |
| Tangent modulus, GPa | 3.12 ± 0.04 | 3.30 ± 0.01 | 3.06 ± 0.06 | 3.21 ± 0.02 | 2.96 ± 0.15 |
| Break elongation, % | >6.5 | 5.3 ± 0.7 | 2.7 ± 0.1 | 3.7 ± 0.4 | 5.7 ± 1.7 |
| 93° C. wet flexural (ASTM D-790): | | | | | |
| Yield strength, MPa | 74 ± 1 | 35 ± 7 | 67 ± 3 | 70 ± 3 | 71 ± 4 |
| Tangent modulus, GPa | 2.62 ± 0.04 | 2.59 ± 0.05 | 2.36 ± 0.14 | 2.55 ± 0.06 | 2.41 ± 0.24 |
| Break elongation, % | 5.9 ± 0.5 | 3.0 ± 0.2 | 4.2 ± 0.3 | 3.5 ± 0.3 | >5.1 |
| Compact tension fracture toughness, $K_q$, MPa-m$^{\frac{1}{2}}$ (ASTM E 399-83) | 2.47 ± 0.29 | 2.12 ± 0.04 | 1.23 ± 0.06 | 1.67 ± 0.07 | 1.48 ± 0.05 |
| Dielectric constant, 1 MHz (ASTM D229/15) | 3.20 | 2.91 | 2.97 | 3.01 | 3.15 |
| Dissipation factor, 1 MHz (ASTM D229/15) | 0.0143 | 0.0132 | 0.0193 | 0.0102 | 0.0112 |
| 93° C. H$_2$O pickup, %: | | | | | |
| 1 day | 2.25 | 1.63 | 2.07 | 1.85 | 1.73 |
| 2 weeks | 3.60 | 2.76 | 3.39 | 2.84 | 2.52 |
| Room temp. methyl ethyl ketone pickup, %: | | | | | |
| 1 day | 0 | 1.14 | 0 | 0 | 0 |
| 2 weeks | 0 | 18.2 | 1.09 | 0 | 0 |
| Room temp. CH$_2$Cl$_2$ pickup, %: | | | | | |
| 1 day | 249 | disint. | disint. | disint. | 62.3 |
| 2 weeks | disint. | | | | disint. |

$^a$Weight of non(DMCB-BMI) component as part of total formulation weight. Acrylates (but not methacrylates) were considered as diene-reactive, with two acrylate double bonds having the potential to react with one molecule of DMCB. For mixtures containing acrylates, an extra amount of DMCB to react stoichiometrically with the acrylate (over the amount needed for a 1:1 stoichiometric reaction with the bismaleimide) was included in the mixture and was counted as part of the non (DMCB-BMI) component. Only the 1,2-isomer contained in the crude 1,2-dimethylenecyclobutane distillate was considered as part of total system solids. Other components in the distillate were made up primarily of the Diels-Alder unreactive 1,3-isomer and were not counted as contributing to solids.

I claim:

1. A composition comprising
   (a) a difunctional bisimide of an unsaturated dicarboxylic acid;
   (b) a polyacrylate monomer; and
   (c) a 1,2-dialkylidenecyclobutane represented by the structural formula

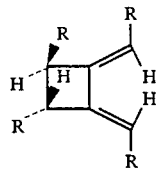

in which each R is selected independently from the group consisting of hydrogen, C$_{1-10}$ alkyl, halo, aryl, alkoxy, aryloxy, alkylthio, arylthio and dialkylamino.

2. The composition of claim 1 in which the polyacrylate monomer is a di-, tri- or tetra- acrylate or methacrylate ester of an aliphatic polyhydric alcohol.

3. The composition of claim 2 in which component (a) is a bismaleimide.

4. The composition of claim 3 in which component (c) is 1,2-dimethylenecyclobutane.

5. The composition of claim 4 in which the equivalent ratio of the 1,2-dimethylenecyclobutane to the (polyacrylate + bisimide) is within the range of about 0.5:1 to about 2:1.

6. The composition of claim 1 in which component (a) comprises 4,4'-bismaleimidodiphenylmethane and component (c) is 1,2-dimethylenecyclobutane.

7. The composition of claim 3 which further comprises an effective amount of a free radical inhibitor for the bismaleimide.

8. The composition of claim 1 which further comprises a fibrous reinforcing agent.

9. The composition of claim 1 which further comprises particulate silica.

10. A polymeric composition comprising the product of contacting, at a temperature of at least about 150° C., monomers comprising
    (a) a bisimide of an unsaturated dicarboxylic acid;
    (b) a polyacrylate monomer; and
    (c) a 1,2-dialkylidenecyclobutane.

11. The composition of claim 10 in which the equivalent ratio of the dialkylidenecyclobutane to the (polyacrylate + bisimide) is within the range of about 0.4:1 to about 0.6:1.

12. The composition of claim 10 in which component (a) is a bismaleimide and component (c) is 1,2-dimethylenecyclobutane.

13. A prepreg comprising the composition of claim 10 and a fibrous substrate.

14. A process for preparing a copolymer comprising the steps of
    (a) preparing a mixture of a difunctional bisimide of an unsaturated dicarboxylic acid, a polyacrylate monomer and a 1,2-dialkylidenecyclobutane represented by the formula

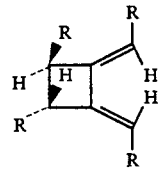

in which each R is selected independently from the group consisting of hydrogen, C$_{1-10}$ alkyl, halo, aryl, alkoxy, aryloxy, alkylthio, arylthio and dialkylamino; and
    (b) heating said mixture to a temperature within the range of about 180° to about 350° C. for at least about 1 hour.

15. The process of claim 14 in which the difunctional bisimide comprises bis(4-maleimidophenyl)methane.

16. The process of claim 15 in which the difunctional bisimide further comprises at least one of 2,4-bismaleimidotoluene and 1,3-bismaleimidobenzene.

* * * * *